United States Patent [19]
Ek

[11] Patent Number: 5,935,149
[45] Date of Patent: Aug. 10, 1999

[54] SUTURING TISSUE

[75] Inventor: Steven W. Ek, Bolton, Mass.

[73] Assignee: Smith & Nephew Inc., Andover, Mass.

[21] Appl. No.: 08/915,758

[22] Filed: Aug. 21, 1997

Related U.S. Application Data

[63] Continuation-in-part of application No. 08/783,126, Jan. 14, 1997, abandoned, which is a continuation-in-part of application No. 08/605,767, Feb. 22, 1996, abandoned, which is a continuation-in-part of application No. 08/603,859, Feb. 22, 1996, Pat. No. 5,730,747, which is a continuation-in-part of application No. 08/479,514, Jun. 7, 1995, abandoned.

[51] Int. Cl.$^6$ .................................................. A61B 17/04
[52] U.S. Cl. ........................................... 606/232; 606/148
[58] Field of Search ................................ 606/72, 73, 75, 606/139, 144, 145, 148, 232

[56] References Cited

U.S. PATENT DOCUMENTS

| | | |
|---|---|---|
| 919,138 | 4/1909 | Drake et al. . |
| 1,037,864 | 9/1912 | Carlson et al. . |
| 1,635,066 | 7/1927 | Wells . |
| 1,815,725 | 7/1931 | Pilling et al. . |
| 2,610,631 | 9/1952 | Calicchio . |
| 2,665,597 | 1/1954 | Hill . |
| 2,880,728 | 4/1959 | Rights ..................................... 128/326 |
| 3,013,559 | 5/1961 | Thomas . |
| 3,349,772 | 10/1967 | Rygg ....................................... 128/340 |
| 3,470,875 | 10/1969 | Johnson . |
| 3,541,591 | 11/1970 | Hoegerman ............................. 128/335 |
| 3,638,653 | 2/1972 | Berry . |
| 3,664,345 | 5/1972 | Dabbs et al. ........................... 128/335 |
| 3,752,516 | 8/1973 | Mumma . |
| 3,840,017 | 10/1974 | Violante . |

(List continued on next page.)

FOREIGN PATENT DOCUMENTS

| | | |
|---|---|---|
| 0 270 705 A1 | 6/1988 | European Pat. Off. . |
| 0 340 159 A1 | 3/1989 | European Pat. Off. . |
| 0 409 364 A2 | 1/1991 | European Pat. Off. . |
| 0 502 509 A1 | 9/1992 | European Pat. Off. ........ A61B 17/00 |
| 0 574 707 A1 | 12/1993 | European Pat. Off. . |
| 0 591 991 A2 | 4/1994 | European Pat. Off. ........ A61B 17/00 |
| WO 95/02363 | 1/1995 | WIPO . |
| WO 95/32670 | 7/1995 | WIPO ............................. A61B 17/00 |
| WO 95/29637 | 11/1995 | WIPO ............................. A61B 17/00 |

OTHER PUBLICATIONS

Innovasive Devices, Inc., Product Information Sheet, ROC Fastener System.
PCT Search Report dated 29 Aug. 1996.
Smith & Nephew Dyonics, Product Advertisement for Pro-line Reusable Endoscopic Hand Instruments.
Auto Suture Company, Product Advertisement, "Endoscopic suturing made easy", 1994.
Smith & Nephew Dyonics, Product Advertisement for Pro-line Reusable Endoscopic Hand Instruments.
Auto Suture Company, Product Advertisement, "Endoscopic suturing made easy", 1994.

*Primary Examiner*—Michael Buiz
*Assistant Examiner*—Daphna Shai
*Attorney, Agent, or Firm*—Fish & Richardson P.C.

[57] ABSTRACT

A method of suturing using a suture with an attached needle includes placing the suture at a desired site to be sutured by passing the needle from a first member of a suture passing forceps to a second member of the forceps. The suture is then secured at the site by passing the needle through a suture receiving passage in an outer member of a suture securing device to position a portion of the suture therein, and inserting an inner member of the suture securing device into the passage to secure the portion of the suture between the inner and outer members. The needle is passed through the passage by threading the needle through a suture threader disposed in the passage, and pulling the threader from the passage. The suture threader has one end terminating in the needled suture and an opposite end terminating in a suture receiving loop.

9 Claims, 11 Drawing Sheets

5,935,149
Page 2

U.S. PATENT DOCUMENTS

| | | | |
|---|---|---|---|
| 3,842,840 | 10/1974 | Schweizer . | |
| 3,871,379 | 3/1975 | Clarke . | |
| 3,901,244 | 8/1975 | Schweizer . | |
| 3,910,281 | 10/1975 | Kletschka et al. | 128/335 |
| 3,946,740 | 3/1976 | Bassett . | |
| 3,976,079 | 8/1976 | Samuels et al. | 128/335 |
| 4,161,951 | 7/1979 | Scanlan, Jr. | 128/340 |
| 4,164,225 | 8/1979 | Johnson et al. . | |
| 4,224,947 | 9/1980 | Fukuda . | |
| 4,235,238 | 11/1980 | Ogiu et al. | 128/334 |
| 4,287,807 | 9/1981 | Pacharis et al. . | |
| 4,291,698 | 9/1981 | Fuchs et al. | 128/335 |
| 4,312,337 | 1/1982 | Donohue . | |
| 4,493,323 | 1/1985 | Albright et al. . | |
| 4,532,926 | 8/1985 | O'Holla | 128/334 |
| 4,573,844 | 3/1986 | Smith . | |
| 4,596,249 | 6/1986 | Freda et al. . | |
| 4,602,635 | 7/1986 | Mulhollan et al. . | |
| 4,621,640 | 11/1986 | Mulhollan et al. . | |
| 4,641,652 | 2/1987 | Hutterer et al. . | |
| 4,643,178 | 2/1987 | Nastari et al. . | |
| 4,669,473 | 6/1987 | Richards et al. | 128/334 |
| 4,741,330 | 5/1988 | Hayhurst | 128/92 |
| 4,744,353 | 5/1988 | McFarland | 128/92 |
| 4,750,492 | 6/1988 | Jacobs | 128/335 |
| 4,779,616 | 10/1988 | Johnson . | |
| 4,781,190 | 11/1988 | Lee . | |
| 4,890,615 | 1/1990 | Caspari et al. . | |
| 4,923,461 | 5/1990 | Caspari et al. . | |
| 4,957,498 | 9/1990 | Caspari et al. . | |
| 4,961,741 | 10/1990 | Hayhurst . | |
| 5,078,731 | 1/1992 | Hayhurst | 606/232 |
| 5,084,058 | 1/1992 | Li . | |
| 5,087,263 | 2/1992 | Li . | |
| 5,100,415 | 3/1992 | Hayhurst . | |
| 5,100,418 | 3/1992 | Yoon et al. . | |
| 5,100,421 | 3/1992 | Christoudias . | |
| 5,133,723 | 7/1992 | Li et al. . | |
| 5,149,329 | 9/1992 | Richardson . | |
| 5,163,946 | 11/1992 | Li . | |
| 5,176,691 | 1/1993 | Pierce . | |
| 5,181,919 | 1/1993 | Bergman et al. . | |
| 5,192,287 | 3/1993 | Fournier et al. . | |
| 5,201,744 | 4/1993 | Jones . | |
| 5,217,471 | 6/1993 | Burkhart . | |
| 5,222,508 | 6/1993 | Contarini . | |
| 5,224,946 | 7/1993 | Hayhurst | 606/72 |
| 5,224,955 | 7/1993 | West | 606/226 |
| 5,234,443 | 8/1993 | Phan et al. . | |
| 5,234,444 | 8/1993 | Christoudias . | |
| 5,250,054 | 10/1993 | Li . | |
| 5,250,055 | 10/1993 | Moore et al. . | |
| 5,257,637 | 11/1993 | El Gazayerli . | |
| 5,259,846 | 11/1993 | Granger et al. | 606/224 |
| 5,261,917 | 11/1993 | Hasson et al. . | |
| 5,268,001 | 12/1993 | Nicholson et al. | 606/72 |
| 5,269,783 | 12/1993 | Sander . | |
| 5,269,791 | 12/1993 | Mayzels et al. . | |
| 5,281,234 | 1/1994 | Wilk et al. . | |
| 5,382,257 | 1/1995 | Lewis et al. | 606/148 |
| 5,387,221 | 2/1995 | Bisgaard | 606/148 |
| 5,389,103 | 2/1995 | Melzer et al. | 606/144 |
| 5,417,712 | 5/1995 | Whittaker et al. | 606/232 |
| 5,425,860 | 6/1995 | Lizardi et al. | 606/232 |
| 5,454,823 | 10/1995 | Richardson et al. | 606/148 |
| 5,464,427 | 11/1995 | Curtis et al. | 606/232 |
| 5,480,403 | 1/1996 | Lee et al. . | |
| 5,486,197 | 1/1996 | Le et al. . | |
| 5,571,090 | 11/1996 | Sherts . | |
| 5,573,548 | 11/1996 | Nazre et al. | 606/232 |
| 5,578,044 | 11/1996 | Gordon et al. . | |
| 5,584,835 | 12/1996 | Greenfield | 606/72 |
| 5,643,321 | 7/1997 | McDevitt . | |
| 5,645,552 | 7/1997 | Sherts . | |
| 5,649,963 | 7/1997 | McDevitt . | |

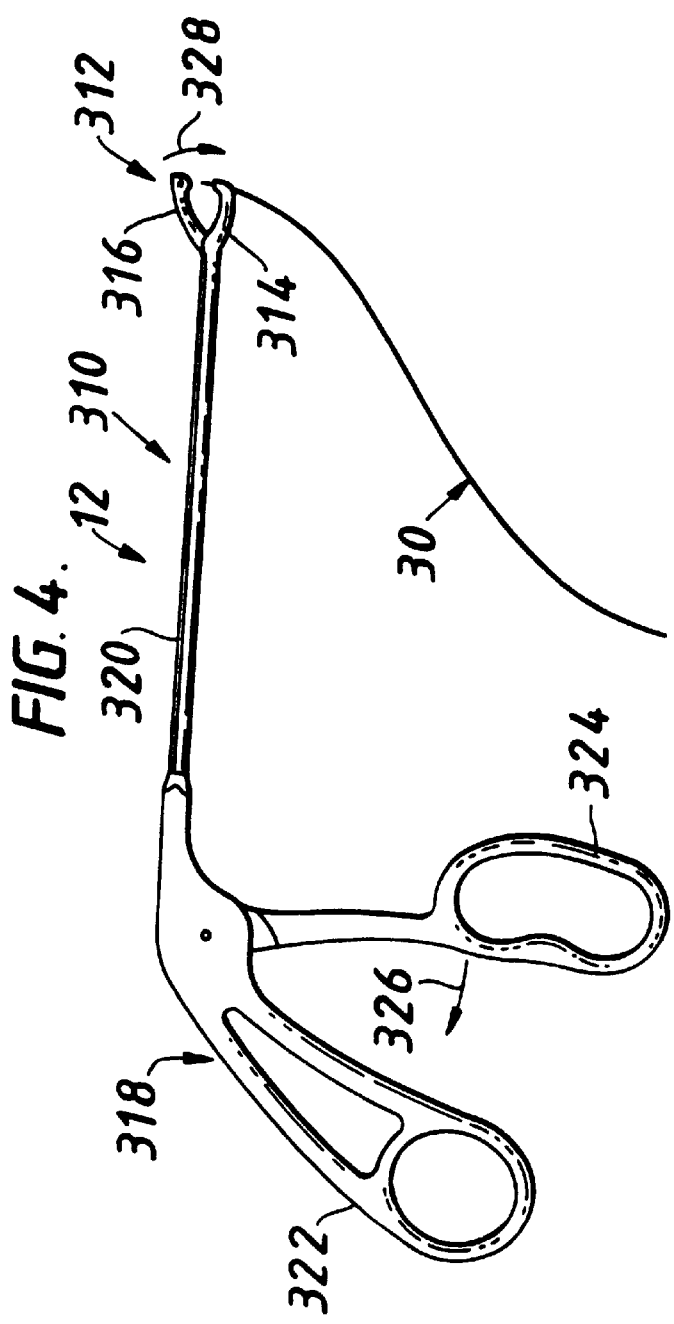
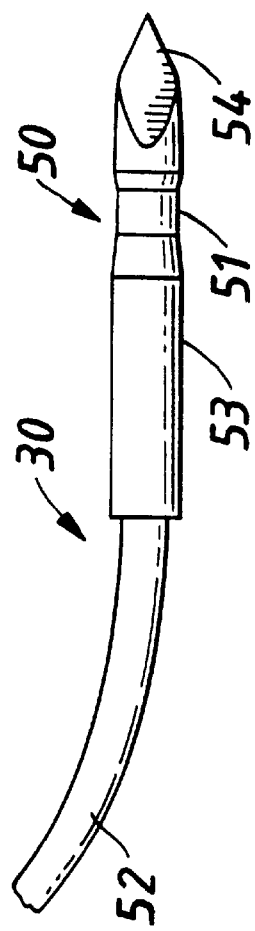

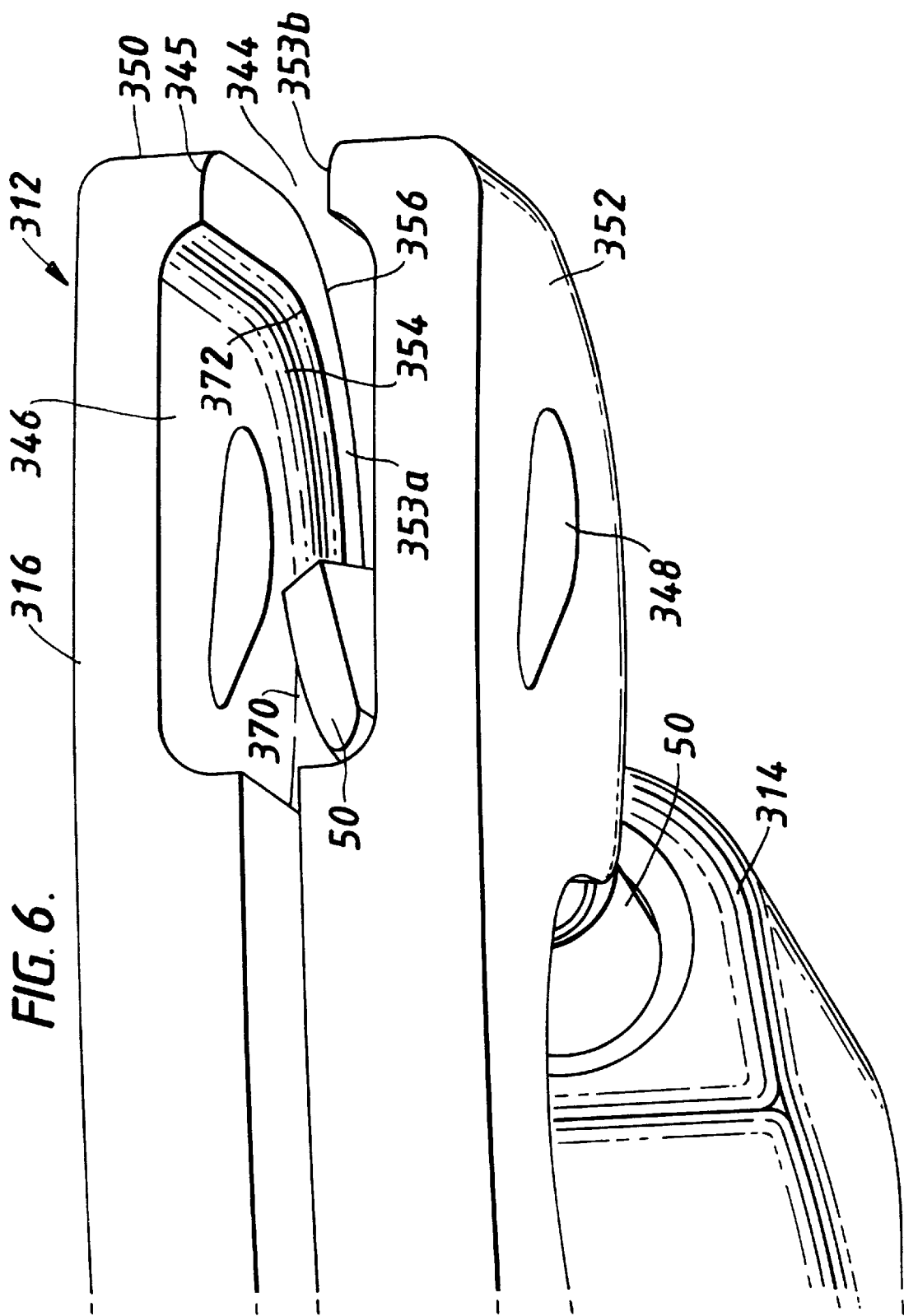

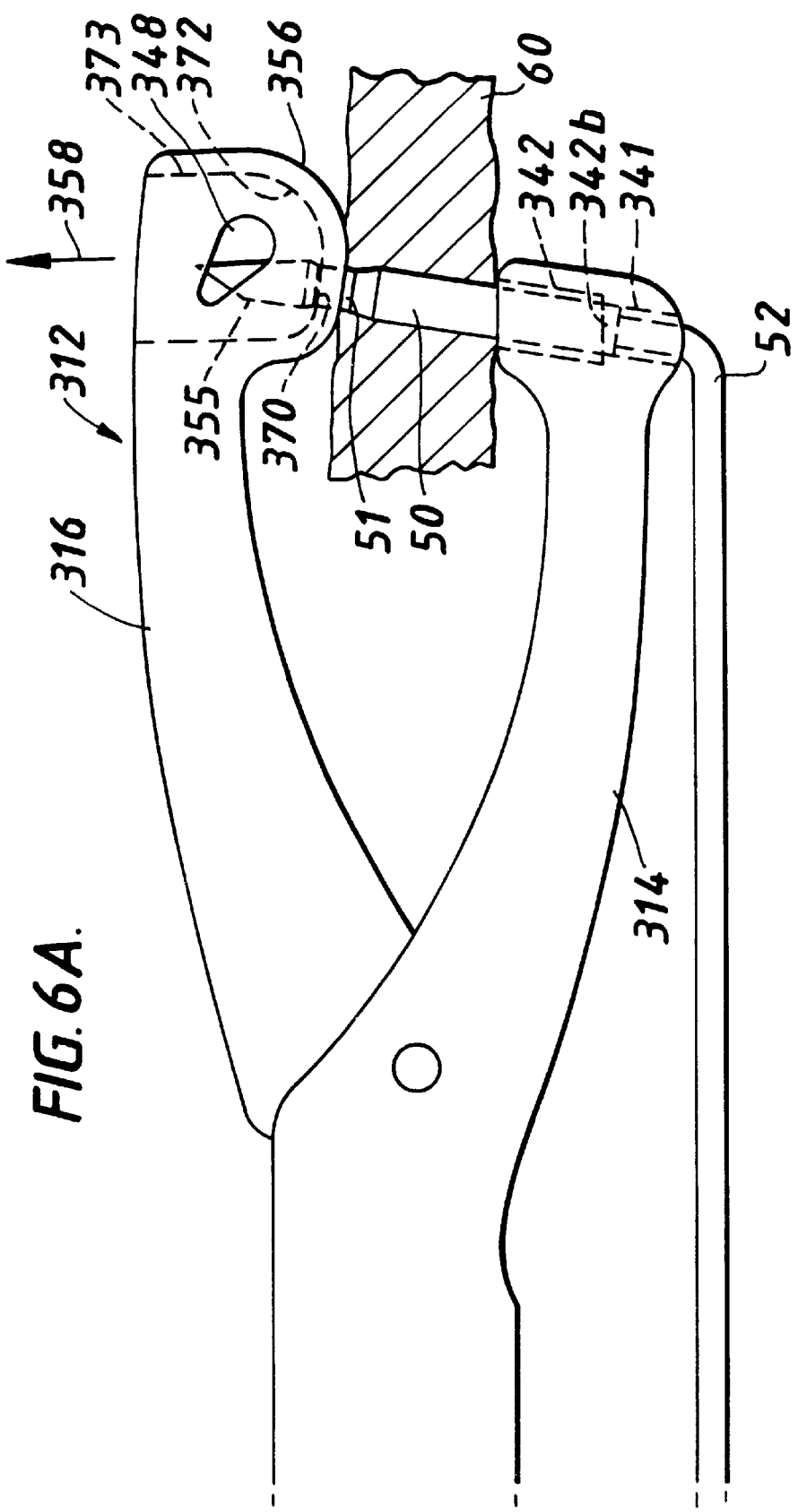

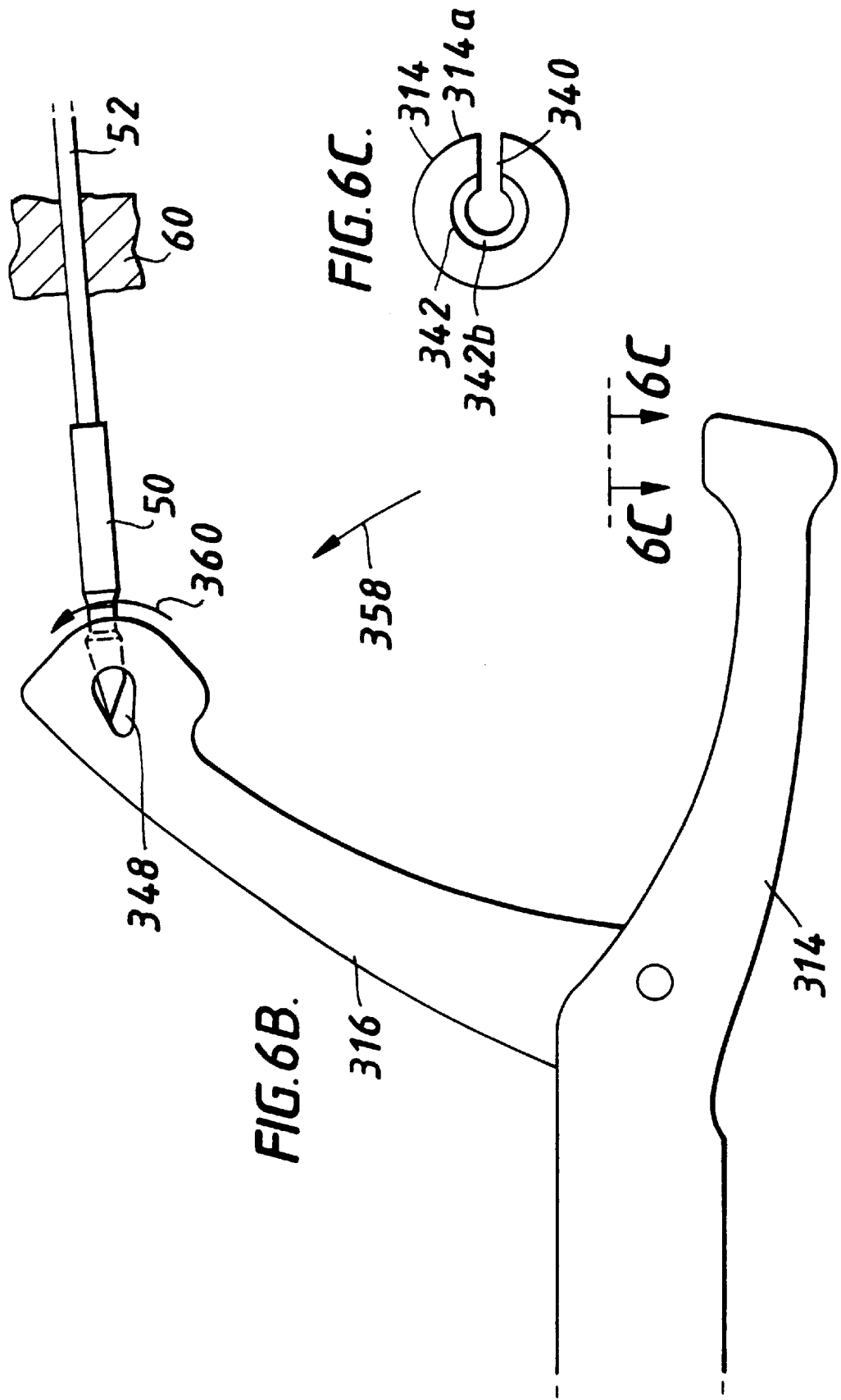

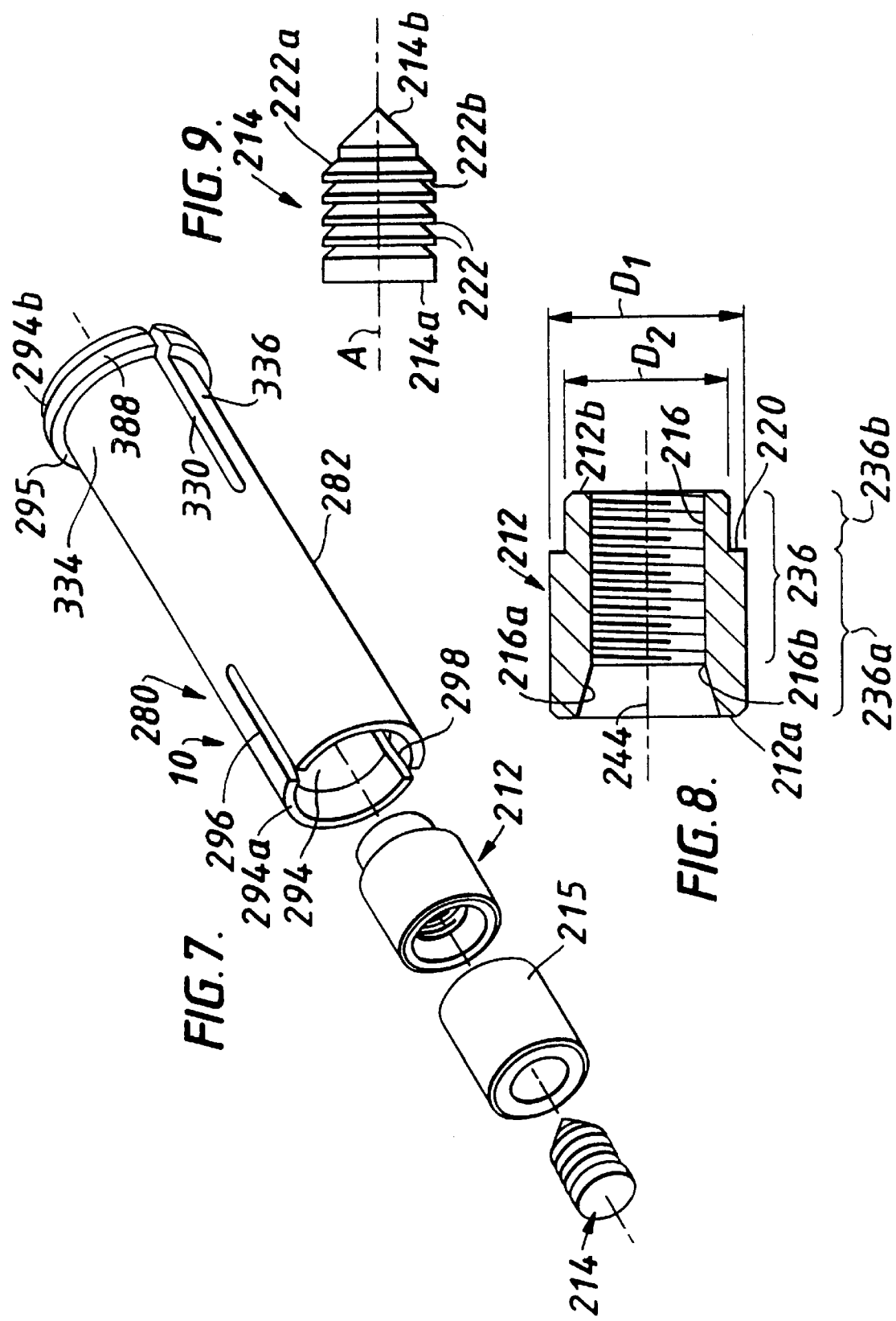

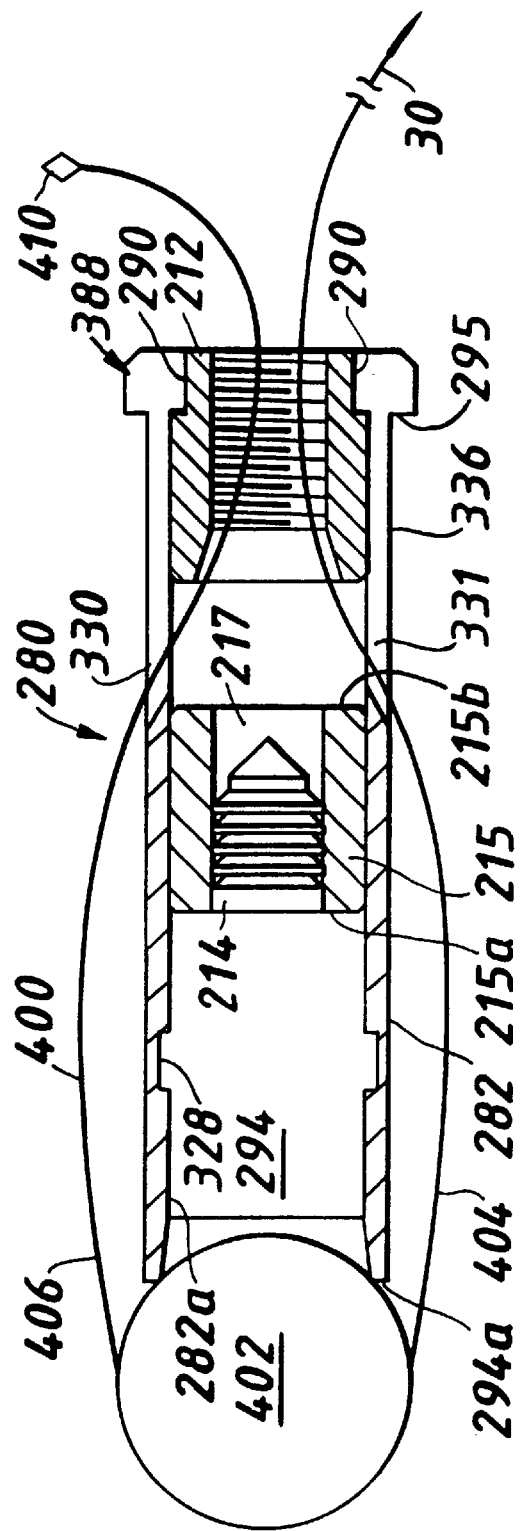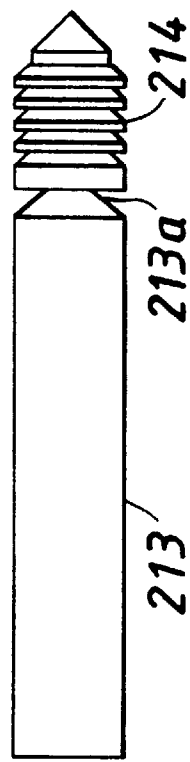

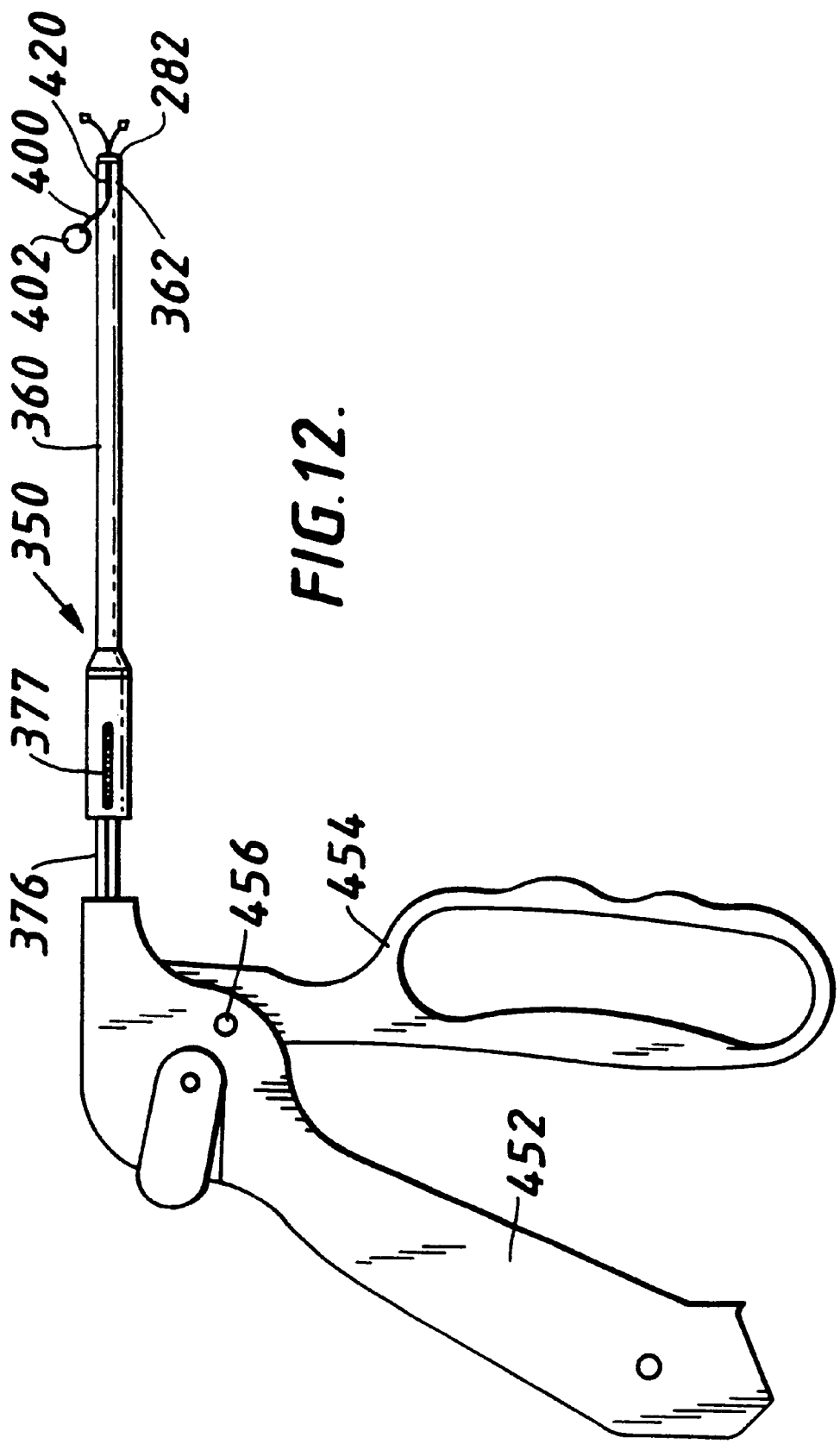

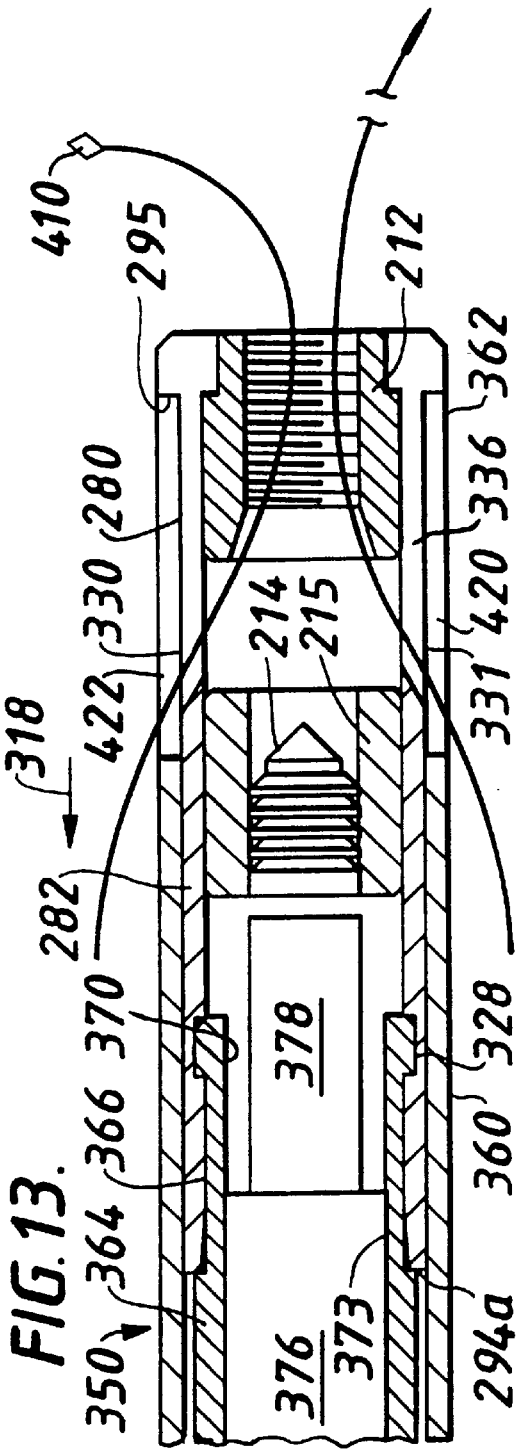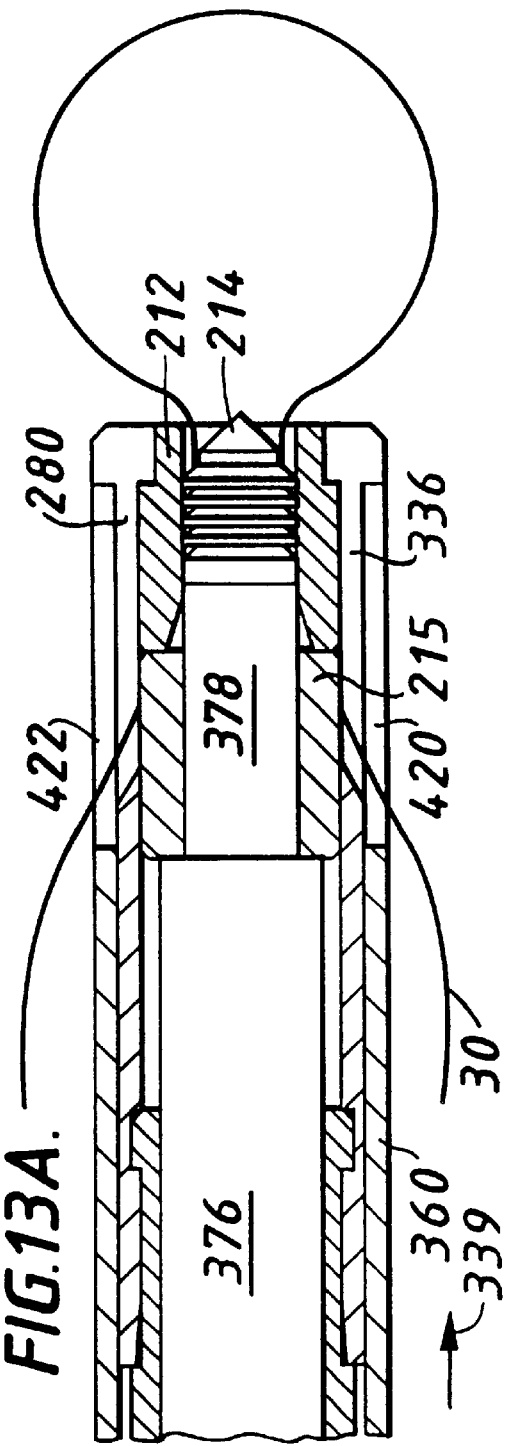

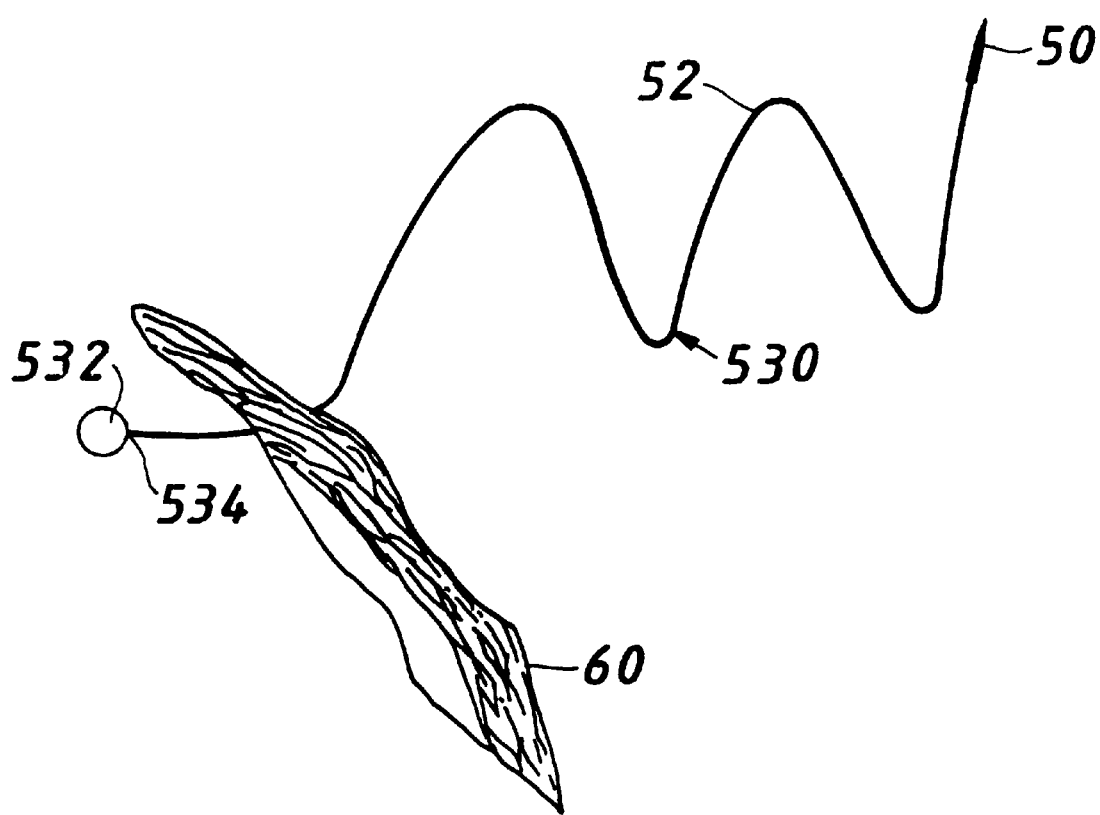

SUTURING TISSUE

CROSS REFERENCE TO RELATED APPLICATIONS

This application is: a continuation-in-part of application Ser. No. 08/783,126, filed Jan. 14, 1997, now abandoned, which is a continuation-in-part of application Ser. No. 08/605,767, now abandoned, filed Feb. 22, 1996, now U.S. Pat. No. 5,730,747; and a continuation-in-part of application Ser. No. 08/603,859, filed Feb. 22, 1996, which is a continuation-in-part of application Ser. No. 08/479,514, filed Jun. 7, 1995, now abandoned, all hereby incorporated herein by reference.

BACKGROUND OF THE INVENTION

This invention relates to suturing, and more particularly, to a method for placing and securing a suture.

Current methods for placing a suture include attaching the suture to a suture anchor which is anchored in tissue, and passing the suture through slits in a retainer to apply tension to the suture.

Instruments for placing a suture also include forceps having upper and lower jaws with a needle associated with the lower jaw. The jaws are used to punch the needle through the tissue to be sutured and a suture thread is then fed through the needle, passing the suture thread from the lower jaw to the upper jaw. Other suturing instruments have been known in which a needle is pushed out of a lower jaw and through tissue, passed to an upper jaw, and held in place in the upper jaw with a spring.

A traditional method of securing suture is simply by tying a knot in the suture. Alternatively, a suture clamp may be used. In a typical suture clamp, the suture is positioned between an open pair of arms which are then pivoted closed to capture the suture between them.

SUMMARY OF THE INVENTION

According to one aspect of the invention, a method of suturing using a suture with a needle attached to a first end of the suture includes providing a suture passing forceps and a suture securing device. The suture passing forceps has a first member configured to hold the needle of the suture and a second member configured to receive the needle from the first member. The suture securing device has an outer member with a suture receiving passage, and an inner member configured for insertion within the suture receiving passage. The method includes placing the suture at a desired site to be sutured by passing the needle from the first member to the second member, and securing the suture at the desired site. The suture is secured by passing the first end of the suture through the suture receiving passage to position a portion of the suture therein, and inserting the inner member into the suture receiving passage to secure the portion of the suture between the inner member and the outer member.

Embodiments may include one or more of the following features. The step of passing the needle from the first member to the second member includes piercing tissue with the needle or looping the first end of the suture around tissue.

Preferably, securing the suture includes threading the needle through a suture threader disposed in the suture receiving passage, and pulling the suture threader from the suture receiving passage to dispose the suture in the suture receiving passage. The needle is removed from the suture threader prior to pulling the suture threader.

Another aspect of the invention features a suture securing cartridge including a sleeve having an axial bore, a suture securing device with an outer member disposed in the bore at a distal end of the sleeve and an inner member disposed in the bore proximally of the outer member and configured for insertion into a suture receiving passage in the outer member, and a suture threader disposed in the suture receiving passage. The suture threader has one end terminating in the needled suture and an opposite end terminating in a suture receiving loop.

According to another aspect of the invention, a needled suture includes a suture thread, a needle disposed at a first end of the suture thread, and an enlarged member disposed at a second end of the suture thread and configured to prevent passage of the second end through tissue.

The suture passing forceps provides for one step positioning, passing, and retrieving of the suture thread. The suture securing device being pre-attached to the suture thread advantageously permits the placed suture to be threaded by passing only a single end of the suture through the device.

Other features and advantages of the invention will be apparent from the following detailed description, and from the claims.

BRIEF DESCRIPTION OF THE DRAWINGS

FIG. 4 shows the suture passing forceps of FIG. 1 with a needled suture;

FIG. 5 shows a needled suture for use with the suture passing forceps of FIG. 4;

FIG. 6 shows a suturing assembly of the suture passing forceps of FIG. 4;

FIG. 6A shows the suturing assembly of FIG. 6 in a first operative position;

FIG. 6B shows the suturing assembly of FIG. 6 in a second operative position; and FIG. 6C is an end view of a suture holder of FIG. 6B, taken along lines 6C—6C.

FIG. 7 is an exploded perspective view of the suture collet assembly of FIG. 1;

FIG. 8 is a cross-sectional view of an outer member of the suture collet of FIG. 3;

FIG. 9 is a side view of an inner member of the suture collet of FIG. 3;

FIG. 10 is a cross-sectional view of the suture collet assembly of FIG. 7;

FIG. 11 is a side view of the inner member of FIG. 9 shown with an attached extension;

FIG. 12 shows a drive tool for use with the suture collet assembly of FIG. 1;

FIGS. 13–13B show the drive tool in use with the suture collet; and

FIG. 14 shows an alternative embodiment of a needled suture for use with the suture passing forceps of FIG. 4.

DESCRIPTION OF THE PREFERRED EMBODIMENTS

Figure 1:
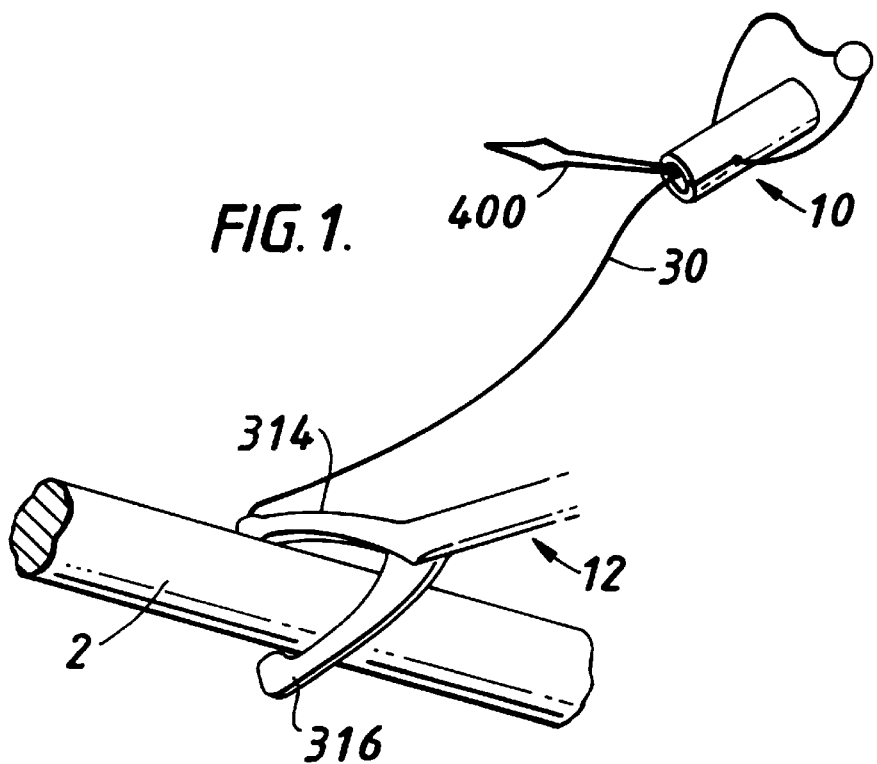
FIG. 1 shows a suture passing forceps and suture collet assembly for placing and securing a needled suture.
Figure 2:
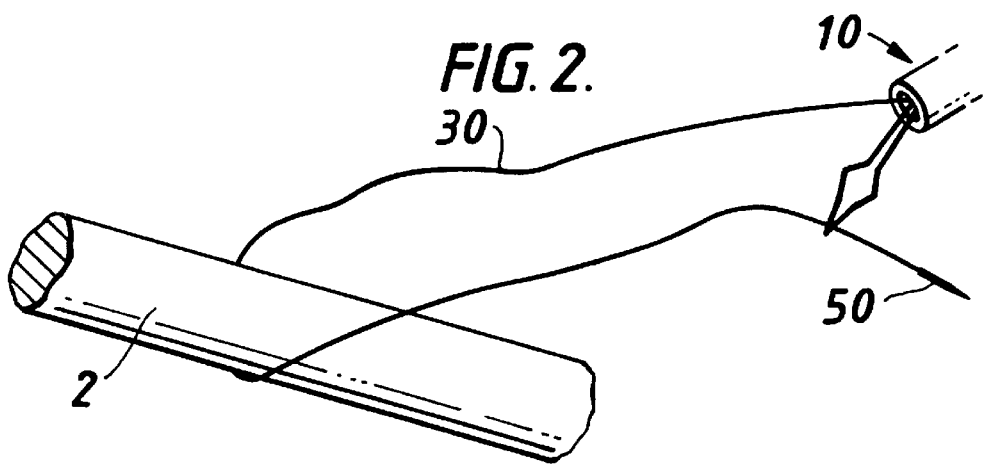
FIG. 2 shows a needled suture placed about a vessel.
Figure 3:
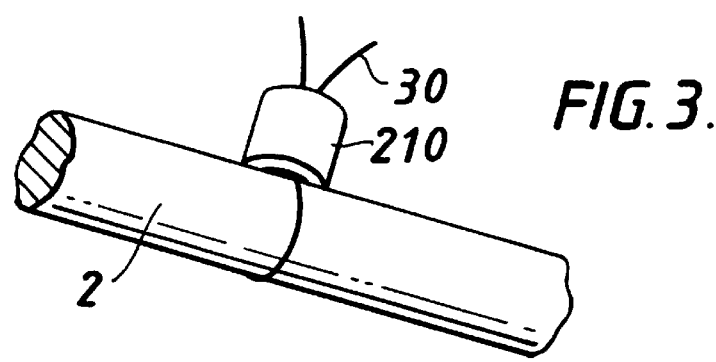
FIG. 3 shows a suture secured with a suture collet of the suture collet assembly of FIG. 1.

Referring to FIG. 1, a suture collet assembly 10 and a suture passing forceps 12 are used to place and secure a suture 30, e.g., when ligating a vessel 2. To place suture 30, a needled end 50 of suture 30 located in a suture holder 314 of suture passing forceps 12 is passed from suture holder 314 to an actuatable member 316 of suture passing forceps 12, as described further below. The needled end 50 of suture 30 is then removed from actuatable member 316 and fed through a suture threader 400 of suture collet assembly 10 (FIG. 2). A suture collet 210 of suture collet assembly 10 is then used to secure suture 30 around vessel 2 (FIG. 3), as described further below.

Referring to FIG. 4, suture passing forceps 12 for use, e.g., in arthroscopic and endoscopic procedures, includes a suturing assembly 312 having suture holder 314 for removably holding needled end 50, and actuatable member 316. Actuatable member 316 is pivotably supported at the distal end of a support shaft 320. A handle 318 connected to the proximal end of support shaft 320 is used to actuate actuatable member 316. Handle 318 includes a stationary thumb section 322 and a movable finger section 324. Movement of finger section 324 in the direction of an arrow 326 moves actuatable member 316 in the direction of an arrow 328 to an operating position adjacent the suture holder 314 (FIG. 6a). The reverse motion of finger section 324 returns actuatable member 316 to its original, open position. An actuation mechanism such as used in the Smith & Nephew Dyonics 2.7 mm. Scoop, product #7204665, may be used. While the illustrated embodiment shows suture holder 314 as stationary and actuatable member 316 pivotably mounted, suture holder 314 can be pivotably mounted and actuatable member 316 stationary.

Referring to FIG. 5, needled suture 30 for use with suture passing forceps 12 includes a needle 50 co-axially aligned with suture thread 52 and attached, e.g., by crimping or clamping, to suture thread 52 at an attachment area 51. Needle 50 includes a substantially straight, tubular shaped body 53 and a pointed distal tip 54 for ease of passage through tissue. The length of needle 50 is less than about 0.5" and preferably about 0.3". Suture thread 52 may be, e.g., #1 or #2 size sutures, monofilament or braided.

Referring to FIGS. 6A and 6C, suture holder 314 includes a through passage 341 defining an enlarged holding region 342 and a needle holding ledge 342b against which needle 50 rests when positioned in suture holder 314. A slot 340 extends from an external surface 314a of suture holder 314 to enlarged region 342. Slot 340 enables complete removal of needled suture 30 from suture holder 14 after passage of the needled suture through tissue.

Referring to FIGS. 6–6C, actuatable member 316 has a window 348 through which needle 50 can be seen. Window 348 enables a user to confirm that the needle has been passed from a suture holder 314 to actuatable member 316. Actuatable member 316 includes first and second member halves 350, 352 having contoured inner surfaces 354 defining a needle holding region 346, and corresponding contoured outer surfaces 356 (only the contoured surfaces of member half 350 being shown). Needle 50 is held, in a passive spring fit, between halves 350, 352 at the edges 353a, 353b (FIG. 6) along a relatively flat region 370 of inner surfaces 354. Inner surfaces 354 also define a contoured region 372. In particular, the suture thread attachment area 51 of needle 50, which has a smaller diameter than a leading section 355 of the needle, is resiliently held in place between opposing edges 353a, 353b. Needle holding region 346 may be created, for example, using electrical discharge machining using a ram shaped to create contoured inner surfaces 354. Halves 350, 352 define an open slot 344 between them into which needle 50 enters and is retained.

Referring particularly to FIGS. 6A and 6B, in use, needle 50 of needled suture 30 is placed in suture holding region 42 by passing thread 52 through slot 340 and pulling on thread 52 to place needle 50 within holding region 342. Suture passing forceps 12 is then manipulated to position tissue 60 between suture holder 314 and actuatable member 316. Handle 318 is actuated moving actuatable member 316 to the operating position shown in FIG. 6A, as needle 50 is pushed through the tissue 60 to be sutured (or around vessel 2). Closing of actuatable member 316 results in attachment area 51 of needle 50 being held within holding region 346 of actuatable member 316. Due to the greater holding force of holding region 346 of actuatable member 316 as compared to the holding force of holding region 342 of suture holder 314, when actuatable member 316 is opened to the position shown in FIG. 6B (moved in the direction of arrow 358), needle 50 is passed from suture holder 314 to actuatable member 316. The entire suturing assembly 312 is pulled away from tissue 60, releasing suture thread 52 from suture holder 314 by passage of suture thread 52 through slot 340 and pulling suture thread 52 through tissue 60.

During the opening motion of actuatable member 316, needle 50 advantageously slides in a pivotal manner within suture holding region 346 along slot 344, allowing needle 50 to align with the suture thread as the thread tugs on the needle. Contoured inner surfaces 354, and particularly contoured region 372, allow the needle to slide within holding region 346 without creating any undesirable loads between needle 50 and member halves 350, 352 which may tend to pull needle 50 from the suture holding region. Additionally, contoured region 372 facilitates removal of needle 50 from actuating member 316 by guiding attachment area 51 of needle 50 in the direction of arrow 360. Needle 50 is guided along inner surfaces 354 of actuating member 316 and exits from the top 345 (FIG. 6) of slot 344 by appropriate manipulation of actuatable member 316 and needled suture 30.

It is desirable that the radius of contoured region 372 be as large as possible while still preserving a length of flat region 370 that is long enough, for example about 0.0411, to initially capture needle 50.

Referring to FIG. 7, suture collet assembly 10 includes a cartridge 280 for carrying suture collet 210. Suture collet 210 includes an outer locking ring 212 and an inner locking pin 214 which securely fasten suture 30 in place within a bore 216 in ring 212 when pin 214 is inserted into bore 216. Cartridge 280 couples to a drive tool, described below, which inserts pin 214 into ring 212.

Referring to FIG. 8, bore 216 is axially-oriented and cylindrical. A portion of the interior surface of ring 212 which defines bore 216 is threaded 236. Bore 216 extends completely through ring 212, from proximal end 212a to distal end 212b, along a longitudinal central axis 244 of ring 212. Bore 216 is tapered 216a from a larger diameter at proximal end 212a to a smaller diameter where threads 236 begin at 216b. Ring 212 has an outer diameter, $D_1$, of 0.123 inches over the majority 236a of its length, and a smaller outer diameter, $D_2$, of 0.105 inches over the remainder 236b of it length. A circumferential ledge 220 is located at the junction of diameters $D_1$ and $D_2$.

Referring to FIG. 9, pin 214 is generally cylindrical in shape and is sized to enter bore 216. A portion of the exterior surface of pin 214 includes a series of axially spaced ridges 222 for lockingly engaging ring threads 236 in a ratchet-like manner when pin 214 is progressively inserted into bore 216 thus securing pin 214 in any one of a plurality of locked positions in ring 212 to secure suture 30 between ring 212 and pin 214 within bore 216.

The circumferentially oriented ridges 222 of pin 214 are axially spaced along pin 214 between proximal end 214a and distal end 214b. The leading (distal) surfaces 222a of ridges 222 are inclined (e.g., at 45 degrees) relative to a longitudinal axis A of pin 214 to slide past threads 236 of ring 212 during insertion, and the trailing (proximal) surfaces 222b of ridges 222 are oriented perpendicular to long axis A to lockingly engaging threads 236 when pin 214 has been inserted by the desired amount. Distal end 214b of pin 214 is conically shaped to help guide pin 214 into bore 216.

The overall size of suture collet 210 with pin 214 inserted into ring 212 corresponds approximately to the size of three successive throws of a suture knot. For example, ring 212 is 0.15 inches long and has a maximum outer diameter of 0.14 inches; pin 214 is only 0.095 inches long (and thus can fit lengthwise entirely within ring 212) and has a maximum outer diameter of 0.045 inches. Ring 212 and pin 214 can be made from a non-absorbable material such as polyacetal available from M. Holland Co., Northbrook, Ill., or a bioabsorbable material, such as Maxon, a polyglyconate, available from Davis & Geck.

Referring to FIGS. 7 and 10, cartridge 280 includes a hollow sleeve 282 with an axial passage 294 extending completely through sleeve 282, from proximal end 294a to distal end 294b. The distal end 294b of sleeve 282 is provided with a pair of axial slots 330, 331 which define a pair of resilient arms 334, 336 which form a clamp 388 to hold suture collet ring 212 in place therebetween. Interior lips 290 on arms 334, 336 form a close fit against the smaller diameter region 236b of ring 212.

Sleeve 282 has proximal slots 296, 298, and a circumferential groove 328 in inner wall 282a of sleeve 282 for purposes to be described. A distal end of arms 334, 336 has an enlarged outer diameter relative to that of the remainder of sleeve 282, such that a shoulder 295 is defined, also for purposes to be discussed.

Pin 214 is supported within passage 294 by a carrier 215. Pin 214 is located within an opening 217 in carrier 215 extending from a proximal end 215a of carrier 215 to a distal end 215b. Carrier 215 acts to center pin 214 within cartridge passage 294.

A suture threader 400 is used to thread suture through ring 212 during operation. A proximal cap 402 is connected to the proximal ends of a pair of suture threader wires 404, 406 which respectively pass through slots 330, 331 and into passage 294. The free ends of wires 404, 406 pass through bore 216 of suture collet ring 212. Wire 406 terminates in a threading loop 410, while wire 404 terminates in suture 30.

To assemble the cartridge assembly of FIG. 10, ring 212 is first placed within passage 294 and slid forward so that ledge 220 engages lip 290. Wires 404, 406 of suture threader 400 are passed through slots 330, 331 and through ring bore 216. Pin 214 is then placed within carrier 215 and carrier 215 with pin 214 are together placed within passage 294 and positioned just proximally of ring 212.

Referring to FIG. 11, to assist in the handling of pin 214, a proximal extension 213 (not shown in FIGS. 7 and 9) is formed on pin 214 which tapers distally to a small neck 213a at proximal end 214a of pin 214. Neck 213a provides for a frangible connection permitting proximal extension 213 to be easily broken off of pin 214 after pin 214 is inserted in carrier 215. With ring 212, pin 214, and carrier 215 in place, cap 402 of suture threader 400 is placed over passage opening 294a to contain the ring, pin and carrier within passage 294. Alternatively, cap 402 can be sized to fit within passage 294 to plug proximal end 294a of cartridge 280.

FIG. 12 illustrates a drive instrument 350 which can be used to emplace suture collet 210 in the body and insert pin 214 into ring 212 to clamp suture in place in the manner discussed above.

Referring also to FIG. 13, instrument 350 has an outer sheath 360 which fits over sleeve 282. A distal end 362 of outer sheath 360 engages shoulder 295 of sleeve 282. Outer sheath 360 includes axial slots 420, 422 aligned with slots 330, 331 for passage of suture 30. A grasper 364 within sheath 360 of instrument 350 has a circumferential groove 366 with a distal ridge 370 configured to fit within groove 328 of sleeve 282, and a shoulder 373 which engages proximal end 294a of sleeve 282 to secure cartridge 280 within instrument 350.

A plunger 376 is slidable within grasper 364 and has a smaller diameter extension 378 which fits within carrier 215 to engage pin 214 and progressively insert pin 214 into passage 216 of ring 212. A spring (not shown), e.g., a torsion spring located in a handle 452 of drive instrument 350, biases plunger 376 away from engagement with pin 214. A second spring 377 acts to bias outer sheath 360 toward engagement with shoulder 295. Alternatively, a position locking mechanism (not shown) can serve to lock outer sheath 360 in position against shoulder 295. Carrier 215 acts to center pin 214 such that plunger 376 squarely engages pin 214. Drive instrument 350 includes handle 452 and a trigger 454 pivotably mounted to handle 452 about pivot pin 456. Plunger 376 is snapped into or permanently mounted to handle 452 and linked to trigger 454 such that movement of trigger 454 controls the movement of plunger 376.

Cartridge 280 with ring 212, pin 214, carrier 215, and suture threader 400 preinstalled as described above, is inserted into instrument 350 by retracting outer sheath 360 proximally (in the direction of arrow 318) to expose grasper groove 366. Cartridge 280, with cap 402 moved aside to expose passage 294, is then inserted onto grasper 364 until distal ridge 370 reaches and snap fits within groove 328. Proximal slots 296, 298 in sleeve 282 permit proximal end 294a of sleeve 282 to widen during insertion of grasper 364. Outer sheath 360 is then returned to the position shown in FIG. 13 with spring 377 acting to maintain engagement of distal end 362 of sheath 360 with shoulder 295 of sleeve 282. Instrument 350 is now ready to install suture collet 210 in the body.

Suture collet 210 is emplaced in the body with cartridge 280 and drive instrument 350 as follows. For example, as a preliminary step, suture 30 is passed around vessel 2 using the suture passing forceps, as discussed above. The user then removes the needled end 50 of suture 30 from actuating member 316, as discussed above, and passes the needled end 50 of suture 30 through threading loop 410. Needled end 50 is then cut off of suture 30. Next, suture threader 400 is moved proximally (arrow 318) using cap 402 to pull suture 30 through suture collet ring 212, slots 330, 331 and slots 420, 422. Instrument 350 is then advanced, for example, through a conventional cannula used in arthroscopic or laproscopic surgery, to the fixation site.

Referring to FIG. 13A, instrument 350 is maneuvered at the surgical site to position suture collet ring 212 as desired (e.g., against the upper surface of vessel 2). Note that in the configuration shown, sheath 360 envelopes all but the distal ends of clamping arms 334, 336, thereby holding them securely in place against suture collet ring 212. The user pulls suture 30 taught and then advances plunger 376 distally (along arrow 339), thereby driving plunger extension 378 distally. Plunger 376 acts to initially slide carrier 215 with pin 214 distally. When carrier 215 contacts ring 212, carrier 215 stops while plunger extension 378 continues to move distally, thereby progressively inserting pin 214 axially into bore 216 of ring 212. Sheath 360 holds cartridge 280 securely in place while pin 214 is being inserted. Pin 214 is progressively inserted into bore 216 until pin 214 reaches a desired locked position in ring 212 securing suture 30 between ring 212 and pin 214.

Figure 13B:
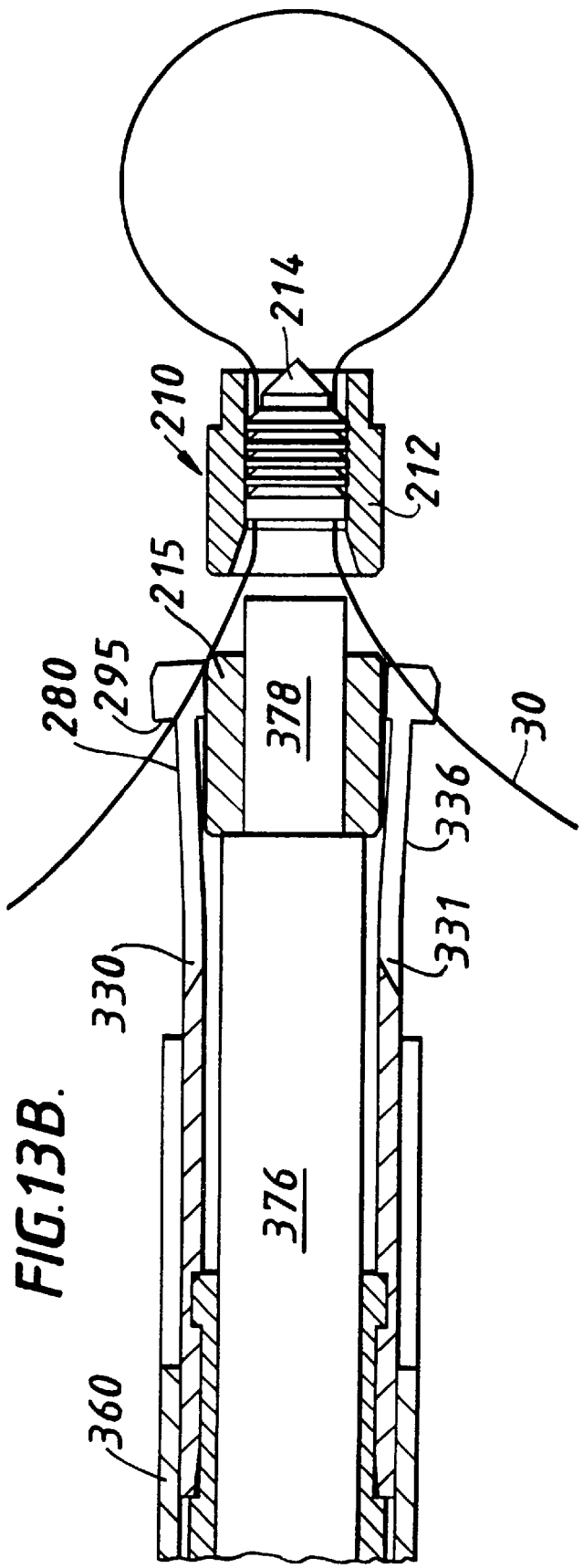

Referring to FIG. 13B, the assembled suture collet 210 is removed from cartridge 280 simply by retracting sheath 360 axially away from shoulder 295 and advancing plunger 376 further distally. With sheath 360 retracted, arms 334, 336 of cartridge 280 flex outwardly as suture collet 210 is moved distally thereby permitting extension 378 to push suture collet 210 distally from cartridge 280. The distance that plunger 376 can be moved distally is limited by travel stops or limits (not shown) located, e.g., in trigger 454 which limit the rotation of trigger 454, such that carrier 215 is not also pushed from cartridge 280. Suture 30 is released from cartridge 280 by passage of suture 30 through slots 330, 331.

The combination of suture passing forceps 12 and suture collet assembly 10 for placing and securing needled suture 30 is particularly attractive to the surgeon because it provides for one step positioning, passing, and retrieving of the suture thread followed by the threading of only a single end of the suture through the collet assembly which then secures the suture simply by actuating the handle assembly of a driver.

Note that the placement of suture 30 within ring 212 acts as the first throw of the suture knot to reduce the tissue and allows sliding travel of the suture much like the first throw of a conventional knot. Frictionless contact between ring 212 and the suture permits the surgeon to feel how much tension is being put into the tissue even more precisely than the first throw of a conventional knot which has some friction. This is particularly advantageous when suturing vessels with thin walls or suturing delicate tissue. In addition, the tension on the suture, instead of acting to pull the suture loose, increases the holding force on the suture applied by suture collet 210.

Suture collet 210 is used in place of conventional securing techniques (e.g., knot tying) to secure suture 30 in place. Suture collet 210 can be used wherever a suture knot would be tied, for example, in ligating branches of vessels, in soft-tissue repair, in reducing tissues, and in securing other types of tissue to bone.

Other embodiments are within the scope of the following claims.

Referring to FIG. 14, in an alternative embodiment, a needled suture 530 for use with suture passing forceps 12, includes needle 50 and thread 52. A suture retaining ball 532 is located at the end 534 of thread 52 opposite needle 50. Suture retaining ball 532 is formed from a biocompatible plastic or metal, e.g., Maxon, Delrin, or an implantable titanium such as Ti6Al-4VELI, to permit suture retaining ball 532 to be implanted in the tissue. In use, needled suture 530 is passed through tissue 60 using suture passing forceps 12, as described above. Suture retaining ball 532 acts to prevent the end 534 of suture thread 52 from passing through tissue 60.

The suture passing forceps described in copending applications Ser. No. 08/832,061, filed Apr. 2, 1997, hereby incorporated herein by reference, Ser. No. 08/603,859, filed Feb. 22, 1996, and Ser. No. 08/479,514, filed Jun. 7, 1995, may also be used to place suture 30. The suture collets, cartridges, and drivers described in copending applications Ser. No. 08/783,126, filed Jan. 14, 1997, and Ser. No. 08/605,767, filed Feb. 22, 1996, may also be used to secure suture 30.

What is claimed is:

1. A method of suturing using a suture with a needle attached at a first end of the suture, comprising:

providing a suture passing forceps having a first member configured to hold the needle of the suture and a second member configured to receive the needle from the first member, providing a suture securing device having an outer member including a suture receiving passage, and an inner member configured for insertion within said suture receiving passage, placing the suture at a desired site to be sutured by passing the needle from the first member to the second member, and securing the suture at the desired site by passing the first end of the suture through said suture receiving passage to position a portion of the suture therein, and inserting said inner member into said suture receiving passage to secure the portion of the suture between said inner member and said outer member.

2. The method of claim 1 wherein said step of passing the needle from the first member to the second member includes piercing tissue with the needle.

3. The method of claim 1 wherein said step of passing the needle from the first member to the second member includes looping the first end of the suture around tissue.

4. The method of claim 1 wherein said step of securing the suture includes threading said needle through a suture threader disposed in said suture receiving passage.

5. The method of claim 4 wherein said step of securing further includes pulling said suture threader from said suture receiving passage to dispose the suture in said suture receiving passage.

6. The method of claim 5 further including removing the needle from the suture prior to pulling the suture threader.

7. A method of suturing using a suture with a needle attached at a first end of the suture, comprising:

providing a suture securing device having an outer member and an inner member configured for insertion within said outer member, said providing including disposing a second end of the suture for securement between said outer member and said inner member, placing the suture at a desired site to be sutured using said needle, and securing the suture at the desired site by positioning the first end of the suture for securement between said outer member and said inner member, and inserting said inner member into said outer member to secure the first end and the second end of the suture between said inner member and said outer member.

8. The method of claim 7 further including providing an instrument having a first member configured to hold the needle of the suture and a second member configured to receive the needle from the first member, said step of placing the suture including passing the needle from the first member to the second member.

9. The method of claim 7 wherein said step of securing the suture includes threading said first end of said suture through a suture threader disposed in a suture receiving passage in said outer member.

* * * * *

UNITED STATES PATENT AND TRADEMARK OFFICE
CERTIFICATE OF CORRECTION

PATENT NO. : 5,935,149
DATED : August 10, 1999
INVENTOR(S) : Steven W. Ek

It is certified that error appears in the above-identified patent and that said Letters Patent is hereby corrected as shown below:

ON THE TITLE PAGE:

Item 56 "OTHER PUBLICATIONS" delete the duplicate entry "Auto Suture Company, Product Advertisement, "Endoscopic suturing made easy", 1994."

On page 2 of the cover of the patent, in the "U.S. Patent Documents" section, replace 5,425,860" with --5,423,860--.

Col. 4, line 38, replace "0.0411" with --0.04"--.

Col. 6, line 41, replace "FIG. 13" with --FIG. 16--.

Signed and Sealed this

Thirty-first Day of October, 2000

Attest:

Q. TODD DICKINSON

Attesting Officer

Director of Patents and Trademarks